United States Patent [19]

Biondi et al.

[11] Patent Number: 5,020,516

[45] Date of Patent: Jun. 4, 1991

[54] CIRCULATORY ASSIST METHOD AND APPARATUS

[75] Inventors: James W. Biondi, North Haven; Richard A. Mentelos, Hamden, both of Conn.

[73] Assignee: Cardiopulmonary Corporation, Branford, Conn.

[21] Appl. No.: 175,810

[22] Filed: Mar. 31, 1988

[51] Int. Cl.⁵ .......................................... A61H 31/02
[52] U.S. Cl. ................................. 128/30.2; 128/671; 128/28; 600/17
[58] Field of Search .............. 128/671, 695, 696, 700, 128/725, 30.2, 28, 24 R, 204.23, 204.24, 64, 668, 713, 716, 718, 719; 600/16, 17

[56] References Cited

U.S. PATENT DOCUMENTS

| 2,241,444 | 5/1941 | Bower | 128/30.2 |
|---|---|---|---|
| 2,529,258 | 11/1950 | Lobo | 128/30.2 |
| 3,212,496 | 10/1965 | Preston | 128/30.2 |
| 3,266,487 | 8/1966 | Watkins et al. | 600/18 |
| 3,303,841 | 2/1967 | Dennis | 128/24 R |
| 3,410,263 | 11/1968 | McGinnis | 600/17 |
| 3,426,743 | 2/1969 | Chesnut et al. | 600/17 |
| 3,430,624 | 3/1969 | Flanagan et al. | 600/17 |
| 3,457,909 | 7/1969 | Laird | 600/17 |
| 3,523,529 | 8/1970 | Kissen | 128/718 |
| 3,587,562 | 2/1968 | Williams | 128/696 |
| 3,730,173 | 5/1973 | Deaton | 128/695 |
| 3,750,644 | 8/1973 | Ragsdale | 600/17 |
| 3,835,845 | 9/1974 | Maher | 128/64 |
| 3,923,055 | 12/1975 | Hammacher | 128/204.23 |
| 3,966,358 | 6/1976 | Heimes et al. | 600/16 |
| 3,985,123 | 10/1976 | Herzlinger et al. | 128/713 |
| 4,016,871 | 4/1977 | Schiff | 128/697 |
| 4,077,402 | 3/1978 | Benjamin, Jr. et al. | 128/24 R |
| 4,204,524 | 5/1980 | Martin et al. | 600/17 |
| 4,316,391 | 2/1982 | Tickner | 128/660.01 |
| 4,448,192 | 5/1984 | Stawitcke et al. | 128/204.26 |
| 4,509,359 | 4/1985 | Gedeon et al. | 128/719 |
| 4,608,995 | 9/1986 | Linnarsson et al. | 128/713 |
| 4,632,107 | 12/1986 | Butler | 128/204.24 |
| 4,646,733 | 3/1987 | Stroh et al. | 128/207.16 |
| 4,676,232 | 6/1987 | Olsson et al. | 128/28 |
| 4,686,974 | 8/1987 | Sato et al. | 128/204.23 |
| 4,753,226 | 6/1988 | Zheng et al. | 128/64 |

Primary Examiner—William E. Kamm
Assistant Examiner—Kennedy J. Schaetzle
Attorney, Agent, or Firm—Gottlieb, Rackman & Reisman

[57] ABSTRACT

Improved cardiocirculatory assistance is provided to a patient by detecting the onset of ventricular ejection in the cardiac cycle of the patient and selectively increasing intrathoracic pressure of the patient in relative phase with respect to the onset of ventricular ejection. Cardiocirculatory output may be monitored and the relative phase of the increase in intrathoracic pressure with respect to the onset of ventricular ejection adjusted to maximize cardiac output. The intrathoracic pressure is increased once every N cardiac cycles where N is a positive integer. The patient interface may include apparatus for supplying high frequency respiration pulses in synchronism with the cardiac cycle. Alternately, or in addition, the pulses may be used to inflate a bladder in contact with the thorax.

25 Claims, 8 Drawing Sheets

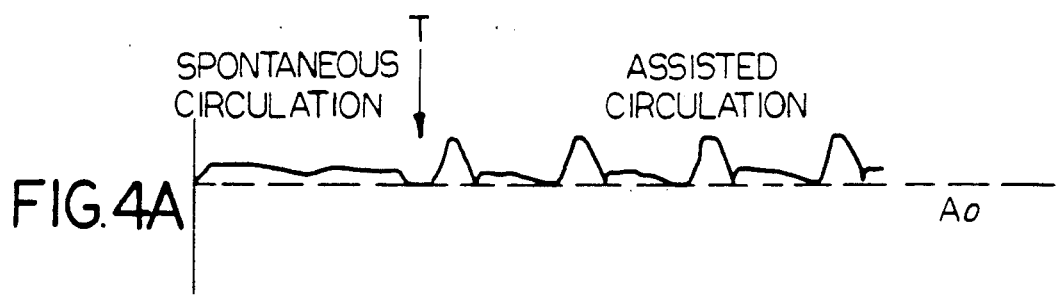
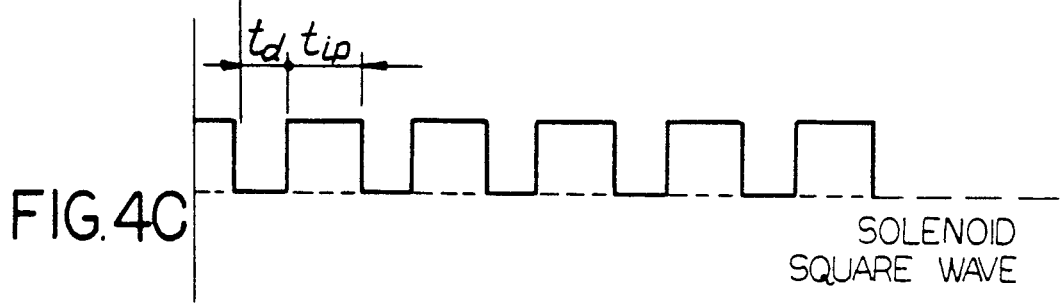
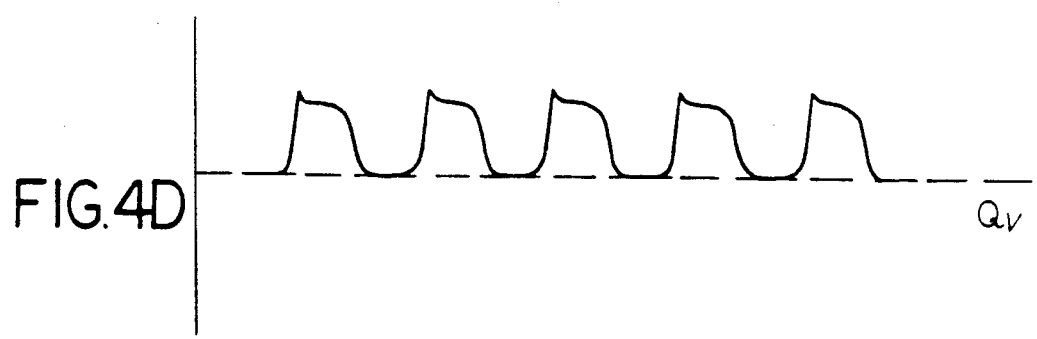
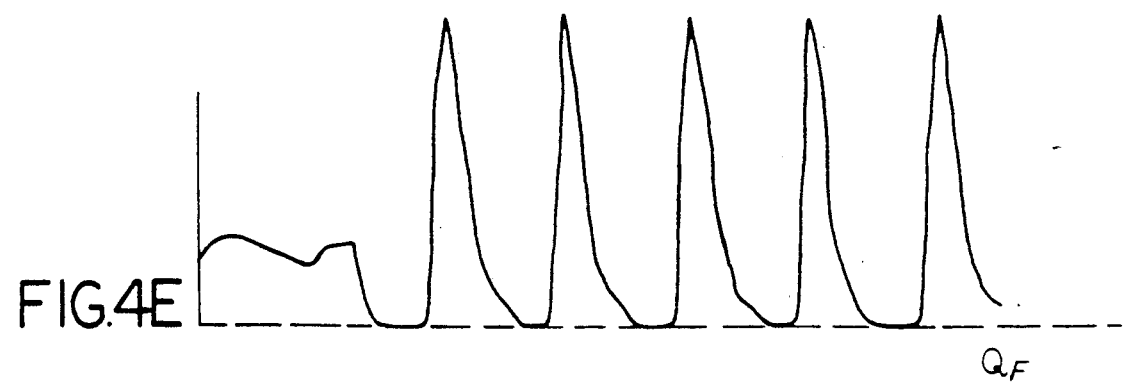

CIRCULATORY ASSIST METHOD AND APPARATUS

TECHNICAL FIELD

This invention relates to apparatus for enhancing circulation in patients having a low level of cardiac output. More particularly, this invention relates to an apparatus and method for enhancing cardiac output by controlling intrathoracic pressure in a manner related to the cardiac cycle of the patient.

BACKGROUND ART

Mechanical inspiration (positive pressure lung inflation), conventionally applied to patients with acute cardio-respiratory failure, distends the lungs, increases airway pressure, and produces an increase in mean intrathoracic pressure. However, the benefit derived by the patient from this increase in functional lung volume is actually offset by the increase in intrathoracic pressure, since the latter produces a decrease in venous return to the heart, a decrease in transmural right atrial pressure (right ventricular filling pressure) and limits right ventricular stroke output. Because the pulmonary circulation serves as a conduit from the right ventricle to the left ventricle and has a high capacitance relative to the right heart, transmural left atrial pressure (left ventricular filling pressure) and left ventricular stroke output are similarly decreased. There is a 2–5 beat phasic delay of this effect relative to the right heart. This is the primary mechanism of decreased cardiac output in all patients during mechanical ventilation in which positive pressure lung inflation is applied either continuously (CPPV) or intermittently (IMV).

In general, cardiac output may be reduced by 50–75% during mechanical ventilation, which may have profound effects on organ blood flow, tissue perfusion, and patient survival. Further, declines in cardiac output will be accentuated in settings of functional hypovolemia, myocardial ischemia and infarction, decreased vasomotor tone, large tidal volume breathing, prolonged inspiratory time, and the application of positive end-expiratory pressure (ubiquitously applied to patients with acute respiratory failure to maintain oxygenation and pulmonary gas exchange).

Changes in aortic pulse pressure and mean arterial blood pressure can also occur during positive pressure inspiration. For example, peak positive pressure inspiration produces a net increase in the series resistance of the pulmonary circulation. Because the pulmonary circulation mechanically couples right and left heart output, an increase in pulmonary vascular resistance, such as that which occurs with conventional low rate, high volume mechanical ventilation (i.e., CPPV, IMV), will impede right ventricular ejection and increase right ventricular dimension and wall stress to produce myocardial ischemia. Decreased right ventricular ejection will decelerate pulmonary blood flow and decrease the filling of the left ventricle, establishing a condition of right and left ventricular interference. This results in decreased left heart preload (decreased left ventricular filling due to left ventricular volume encroachment by the overdistended right ventricle) and decreased left heart ejection. In this way, conventional mechanical ventilation may produce profound cardiocirculatory dysfunction by altering both the series and parallel relationships of right and left ventricular function.

There have been some attempts to alleviate the adverse effects of mechanical inspiration on circulation by momentarily decreasing the pressure of the respiration gas with the aid of a pulse-synchronized signal during the propagation time of the pulse wave in the alveolar flow path, and then immediately re-establishing the pressure that existed prior to the decrease. Proper synchronization of pulses assists in filling of the left atrium of the heart. This is somewhat beneficial, but does not deal with the overall problem of decreased biventricular preload secondary to increased mean intrathoracic pressure.

DISCLOSURE OF THE INVENTION

It is a principal object of the invention to use momentary timed increases in intrathoracic pressure to increase cardiac output.

It is another object of the invention to utilize a mechanical respirator to assist, rather than to depress, cardiac circulation.

It is a further object of the invention to provide pressure impulses to increase intrathoracic pressure at times during the cardiac cycle which will assist, rather than impede, cardiac filling and ejection.

In accordance with the method of the invention, improved cardiocirculatory assistance is provided to a patient by detecting the onset of ventricular ejection in the cardiac cycle of the patient and selectively increasing intrathoracic pressure of the patient in relative phase with respect to the onset of ventricular ejection. The method may further comprise the steps of monitoring cardiocirculatory output and adjusting the relative phase of the increase in intrathoracic pressure with respect to the onset of ventricular ejection to maximize cardiac output. The step of selectively increasing the intrathoracic pressure is performed once every N cardiac cycles where N is a positive integer.

In accordance with the invention, an apparatus for improving the cardiac output of the patient comprises detection means for detecting the onset of ventricular ejection in the cardiac cycle of the patient, pressure increasing means for selectively increasing the intrathoracic pressure of the patient, and control means responsive to the detection means for activating the pressure increasing means in a relative phase with respect to the ventricular ejection. The apparatus may further comprise cardiocirculatory monitoring means for ascertaining the extent to which the apparatus improves cardiac output and for providing an output signal indicative thereof. The apparatus may also include delay means responsive to the output signal for delaying activation of the control means in response to the detection means so that the cardiac output is maximized. The apparatus may also comprise divider means responsive to the detection means for providing an output every N cardiac cycles, in which case the control means is responsive to the divided output.

Thus, in accordance with the invention, the intrathoracic pressure of the patient is increased synchronously with ventricular ejection. This may be accomplished by a mechanical respirator, which also assists in respiration, or by other means such as a bladder surrounding the thorax of the patient or an implant within the thorax.

If mechanical inspiration is shortened to 250–350 msec (so that the entire respiratory cycle occurs within the cardiac cycle) and synchronized to the specific point in the cardiac cycle which marks the onset of ventricular ejection (40–100 msec post-R wave of a continuously recorded ECG), then lung inflation and increases in mean intrathoracic pressure occurring in phase with the cardiac cycle can be used to maintain left ventricular preload and thereby provide a mode of augmented cardiac output. Further, because increases in mean intrathoracic pressure occur during right and left ejection, the transmural pressure gradient (peak ventricular systolic pressure - aortic pressure) against which the myocardium must work is decreased. Thus, ventricular afterload may be reduced and this may result in decreased myocardial wall stress and decreased myocardial oxygen consumption. This mode of ventilation may provide a myocardial sparing effect. Because intrathoracic pressure is at a nadir during the diastolic phase of each cardiac cycle, ventricular preload (filling) is augmented on a beat-to-beat basis. The net effect is increased cardiac output and decreased myocardial work.

BRIEF DESCRIPTION OF DRAWINGS

Further objects, features and advantages of the invention will become apparent upon consideration of the following detailed description in conjunction with the drawings, in which:

FIGS. 4A to 4E illustrate the interrelationship of physiological parameters when a first mode of operation of the system of FIG. 1 is commenced;

DETAILED DESCRIPTION OF THE DRAWINGS

Figure 1:
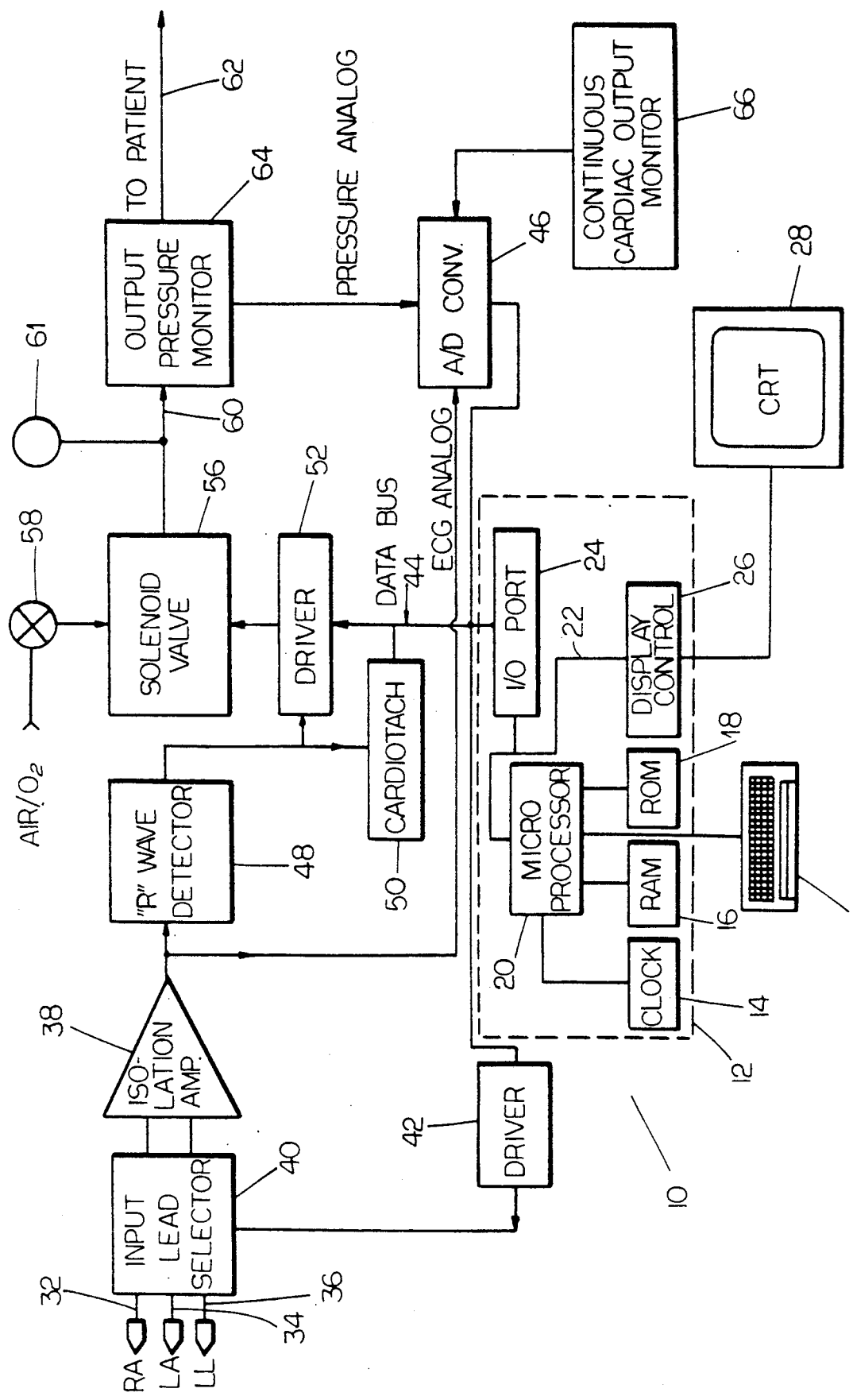
FIG. 1 is a block diagram of an apparatus in accordance with the invention.

Referring to FIG. 1, the system 10 according to the invention provides short duration high frequency air pressure pulses which are synchronized to the cardiac cycle of the patient. The system is controlled by a microcomputer 12. Microcomputer 12 includes a clock 14, a RAM 16, and a ROM 18 connected to microprocessor 20. Microprocessor 20 is interfaced to an internal data bus 22 which is also connected to an input/output port 24. Internal bus 22 is also connected to a display controller 26 which controls a display unit 28 which may be a CRT or other suitable display. As described below with respect to FIGS. 4A to 4E and FIGS. 5A to 5E, waveforms appropriate for enabling a physician or other health care professional to monitor and optimize the operation of the system may be displayed on display unit 28. Further, data and other information entered by means of keyboard 30, and interfaced to microprocessor 20 of microcomputer 12, may also be displayed. Although not shown in FIG. 1, microcomputer 12 may be of the PC type and may have a disk drive (not shown) for additional data storage capability. The disk drive may be of the type that uses floppy disks, thus providing achieving ability. Further, microcomputer 12 may have an interface for a printer.

Electrical signals indicative of a patient's heartbeat are provided to system 10 by electrocardiograph leads. These leads include RA lead 32, LA lead 34 and LL lead 36. Two of these three leads are connected to an isolation amplifier 38 by an input lead selector 40. Isolation amplifier 38 may be any of several well known amplifiers suitable for electrocardiography. Input selector 40 consists of a switching apparatus controlled by logic signals from a driver 42. Driver 42 is connected to an external data bus 44 from port 24. Thus, appropriate entries at keyboard 30, as described below with reference to FIGS. 6A and 6B, may be used to select which two of the three leads 32, 34 and 36 are connected at any particular point in time, to the input of isolation amplifier 38.

The output of isolation amplifier 38 is supplied to an analog-to-digital converter 46. Converter 46, which has an analog multiplexer input, is used to convert more than one analog signal to digital form. Converter 46 has a sufficiently high conversion rate so that all of the inputs can be converted, thus enabling the input signals to be accurately represented in digital form. The digital output of converter 46 is supplied to appropriate input terminals of port 24 by data bus 44. Microprocessor 20 then serves the function of storing the digital signals in RAM 16. These signals are eventually supplied to display controller 26 by internal data bus 22 for use in providing a display on display unit 28.

The output of isolation amplifier 38 is also supplied to R-wave detector 48. R-wave detector 48 includes a conventional peak detector which recognizes a reversal in the sign of the derivative or slope of the signal supplied by isolation amplifier 38 and provides a short digital output pulse when such reversal takes place. Prior to evaluating the wave for such reversal of sign, a filter internal to R-wave detector 48 is used to filter out the P and T waves so that only the frequency components of the QRS complex are passed to the peak detector.

The output of R-wave detector 48 is supplied to a cardiotach circuit 50. Cardiotach circuit 50 provides a digital output on data bus 44 representative of the heart rate of the patient. This may be accomplished by gating the output of R-wave detector 48 into an up/down counter within cardiotach circuit 50 for a predetermined period of time to increase the count, and then gating pulses from a clock of known frequency into the same up/down counter for a predetermined period of time to decrease the count to zero. Such cardiotach circuits are well known in the art.

The output of R-wave detector 48 is also supplied to a solenoid driver circuit 52. Driver circuit 52 operates a solenoid of solenoid controlled valve 56 to open momentarily to permit a quantity of gas from the output of a pressure regulator 58 to pass through valve 56. The high pressure input to regulator 58 is connected to an air or air and oxygen mixture source (not shown) as may be appropriate, depending upon the manner in which system 10 is interfaced to the patient.

Driver circuit 52 responds to signals from microcomputer 12 provided on data bus 44. However, as noted above, the output of R-wave detector 48 is also provided to circuit 52. A pulse from R-wave detector 48 does not, by itself, activate circuit 52. Instead, a predetermined delay interval is started, during which interval, if an appropriate signal is received by circuit 52 by way of data bus 44, driver circuit 52 will activate solenoid 54. Appropriate logic circuitry for performing this function is well known in the art.

The output of valve 56 is connected to a pressure line 60. A pressure reservoir or ballast 61 is also connected to line 60 to provide some smoothing of the air pulses from valve 56, thus providing more comfort for the patient.

Line 60 is connected to an output pressure monitor 64. Monitor 64 includes an appropriate transducer for providing an analog signal representative of the gauge pressure in an output pressure line 62 which is used to interface system 10 to the patient. The analog output of the pressure transducer within monitor 64 is provided to converter 46 for purposes of being converted into a digital format which can be processed by microcomputer 12. Thus, if appropriate data are stored in RAM 16, the analog pressure waveform can be displayed on display unit 28. Further, alarm thresholds can be set to notify the medical staff if a condition that is detrimental to the patient's well-being occurs or to initiate automatic responses to alleviate or correct any such occurrence under the control of a program stored in ROM 18.

A continuous cardiac output monitor 66 (FIG. 2A) provides an analog signal to one input of analog-to-digital converter 46. As is the case for pressure monitor 64, output monitor 66 may be used to provide an alarm function or to initiate predetermined changes in the operation of system 10 if output signals from output monitor 66 are such as to indicate that conditions detrimental to the health of the patient exist.

Figure 2:
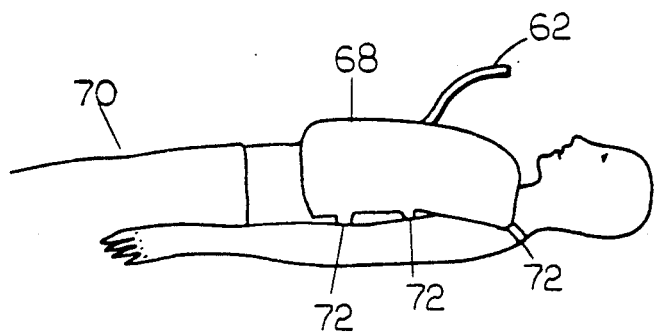
FIG. 2 illustrates a bladder useful for increasing intrathoracic pressure, placed around a patient, the bladder being for use with the system of FIG. 1.

Referring to FIG. 2, output line 62 is connected to an inflatable pressure jacket or bladder 68 which is secured around the thorax of a patient 70 by suitable release straps 72. The use of an inflatable bladder to interface the patient to system 10 is extremely advantageous in that it is completely noninvasive. Bladder 68 can be any of several well known bladders such as those used to treat shock or those used by the pilots of high performance aircraft to control the distribution of blood in the body under conditions of high acceleration. By the proper application of pressure pulses along output line 62, intrathoracic pressure is rhythmically increased at timed intervals related to the cardiac cycle, as more fully described below.

Figure 2A:
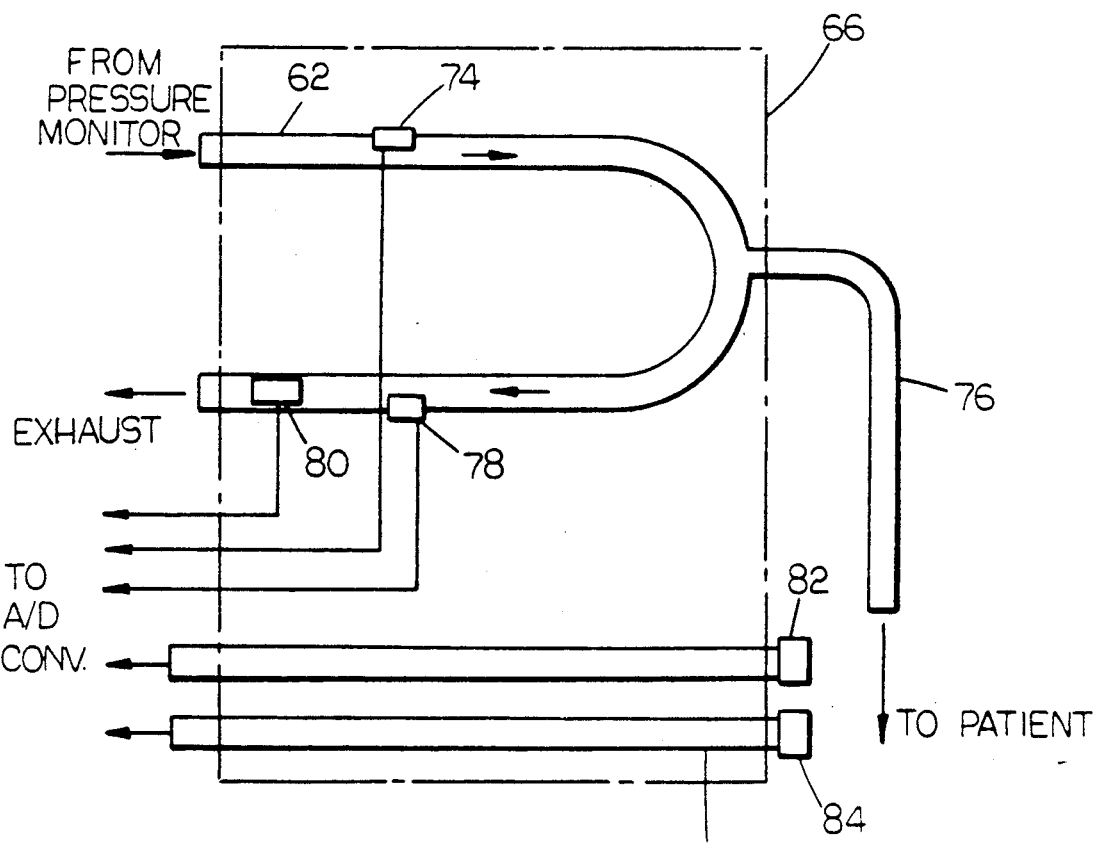
FIG. 2A illustrates components of an embodiment of the continuous cardiac output monitor of FIG. 1.

FIG. 2A illustrates an alternative approach for interfacing system 10 to the patient. This embodiment includes a continuous cardiac output monitor 66. A first oxygen concentration sensor 74 measures the concentration of oxygen in the air/oxygen mixture of line 62. A patient attachment tube 76 which opens into line 62 is in turn connected to an endotracheal tube (not shown) which is used to provide mechanically assisted respiration to the patient. A second oxygen sensor 78 in line 62 determines the concentration of oxygen in the air stream exhausted by tube 62, which is a combination of the air stream from pressure monitor 64 (FIG. 1) and the gas exhausted by the patient's lungs. A flow sensor 80 determines the volume of gas exhausted from tube 62. Flow sensor 80 also serves to provide a small amount of resistance to flow so that when pressure pulses are provided due to the opening of valve 56 (FIG. 1) a portion of the gases of the pulse are forced into the patient's lungs through tube 76 and the endotracheal tube.

Oxygen sensors 74 and 78 may be those associated with a polarographic oxygen analysis system or by techniques of optical fluorescence either of which may provide the actual inputs to microcomputer 12. Flow sensor 80 may be any of several well known devices such as a pneumotach device and is associated with an appropriate electronics package to provide an input to microcomputer 12.

The continuous cardiac output monitor 66 of FIG. 2A also includes a means for determining the difference in arterial and venous blood oxygen concentration. A finger tip pulsed oximeter sensor 82 (with an associated electronics package, not shown) is used to determine arterial blood oxygen content. An optical oxygen concentration sensor 84, positioned in the pulmonary artery, at the end of a pulmonary artery catheter 86 (and an associated electronics package, not shown) is used to determine venous oxygen content.

Signals from first oxygen sensor 74, second oxygen sensor 78, flow sensor 80 and the electronic packages associated with sensors 82 and 84 are all provided to microcomputer 12. Using a variation of Fick's equation, microcomputer 12 monitors, on an almost a breath by breath, i.e., instantaneous, basis, the rate of oxygen uptake and the difference in arterial and venous oxygen concentration to determine cardiac output.

Fick's equation is based on the theory that the uptake or release of a substance by an organ is the product of the blood flow to the organ and the arteriovenous concentration of the substance. This principle, when applied to the lungs, can be stated as: oxygen uptake is equal to the product of blood flow multiplied by the difference in arterial oxygen concentration and venous oxygen concentration. For purposes of cardiac output determinations, the cardiac output is equal to the oxygen consumption of the patient divided by the arterial-venous oxygen concentration difference.

Monitoring is accomplished by multiplying the difference in oxygen concentration at sensor 74 and sensor 78 by the flow rate output of sensor 80 and dividing this product by the difference in arterial and venous oxygen concentration as determined by sensors 82 and 84. Successive quotients are stored in a portion of RAM 16 programmed to operate as a first in/first out memory. When the sum of the values stored falls below a predetermined limit, an alarm is provided, thus indicating that the patient's cardiac output has dropped.

While the continuous cardiac output monitor 66 of FIG. 2A is designed to provide a relatively accurate absolute determination of cardiac output, other systems may be used in place of the apparatus illustrated in FIG. 2A. For example, indications of cardiac output may be provided to microcomputer 12 by an in dwelling optical flow sensor, a Doppler flow probe, an electromagnetic flow meter or an impedance flow sensor. The outputs of these systems also may be averaged over a period of time by suitable integrating means incorporated in microcomputer 12 and operatively associated with the first in/first out memory portion of RAM 16 to provide an averaged representation of cardiac output.

The respiration induced by the patient interface in accordance with FIG. 2A consists of short rapid breaths. This is a marked departure from the operation of conventional respirators wherein the natural breathing cycle of the patient is utilized. The short rapid breaths, if synchronized to cardiac ejection as described below, provide an extremely significant enhancement of cardiac output.

While FIG. 2 and FIG. 2A illustrate, respectively, one completely noninvasive patient interface and one patient respiratory interface which is relatively noninvasive, it will be recognized that other means for increasing intrathoracic pressure are contemplated. For example, an appropriate bladder may be implanted within the thorax of the patient in proximity to the heart so as to increase intrathoracic pressure in accordance with the principles of the invention. However, it will be recognized that this approach entails significant risks due to the necessary surgical procedures.

Figure 3:
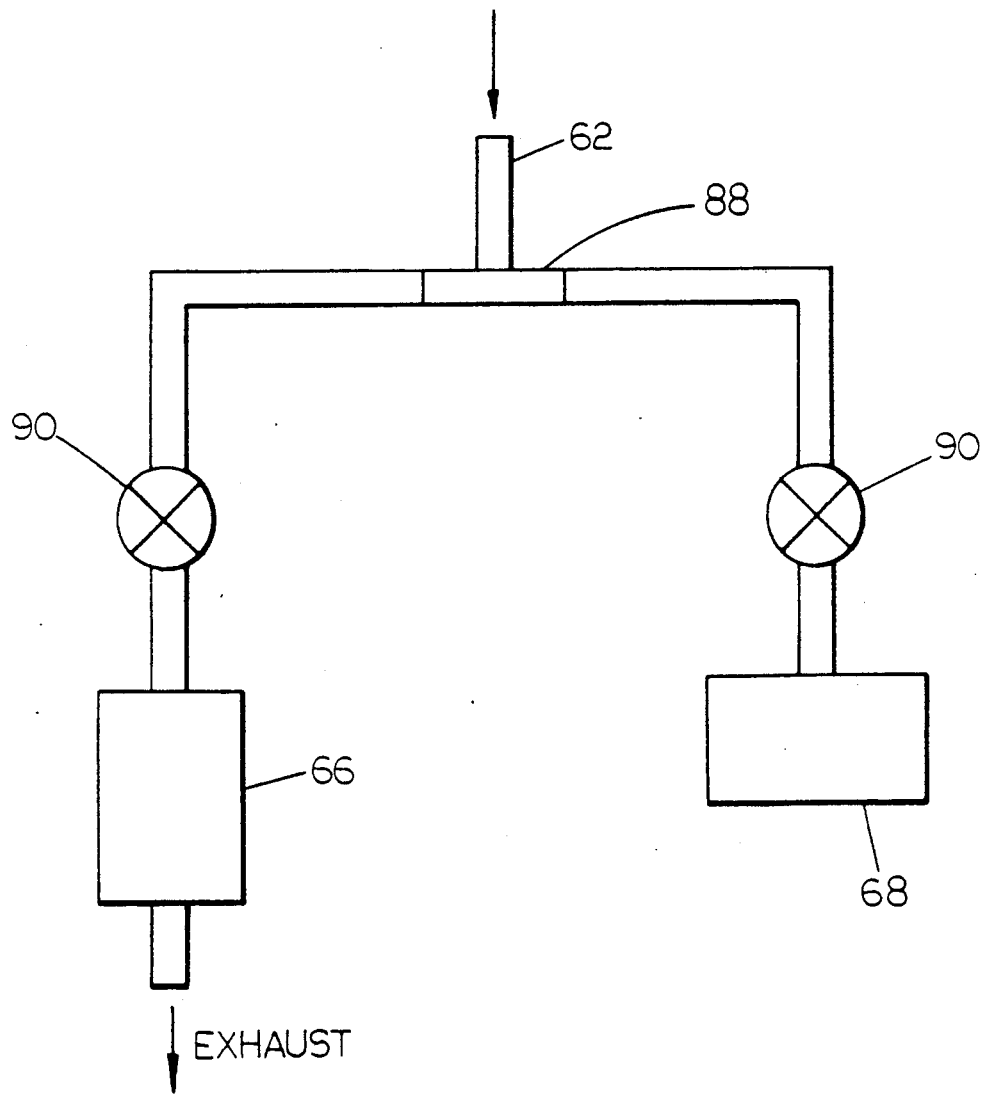
FIG. 3 illustrates the manner in which the apparatus of FIG. 2 and FIG. 2A may be connected to the system of FIG. 1.
Figure 5A:
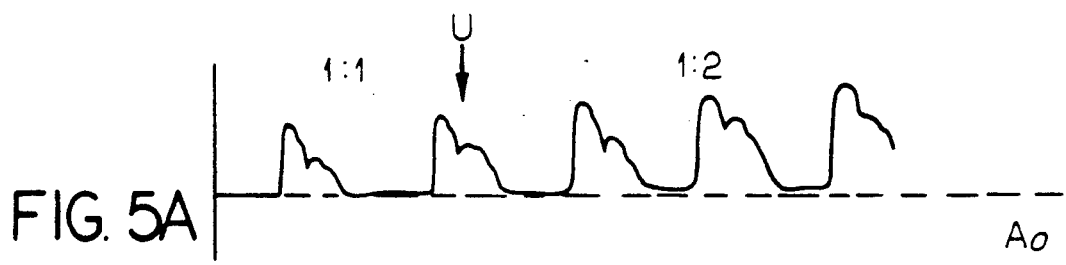
FIGS. 5A to 5E are similar to FIGS. 4A to 4E but illustrate a change from the first mode of operation to a second mode of operation of the system of FIG. 1.
Figure 5B:
Figure 5C:
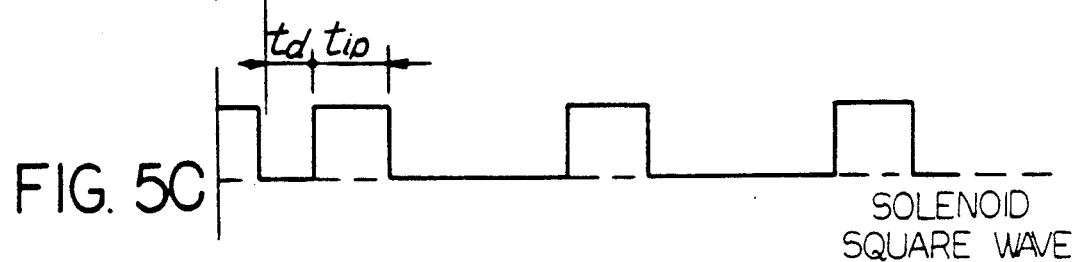
Figure 5D:
Figure 5E:
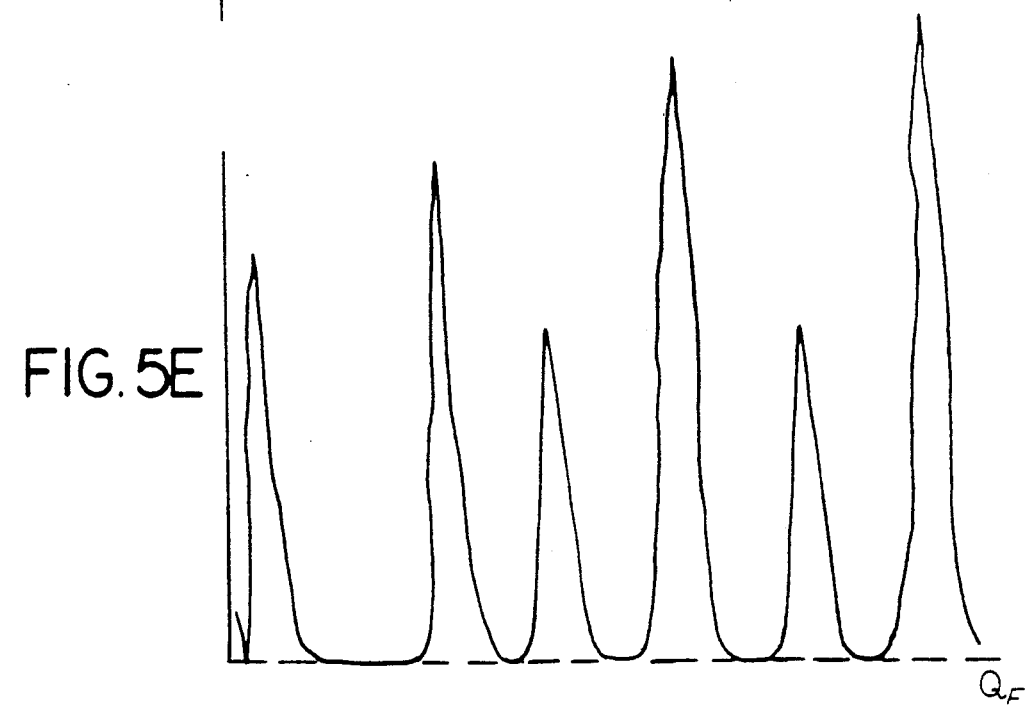

While the manner of interfacing to a patient described in FIG. 2 or FIG. 2A can each be implemented independently, it is also contemplated that both may be used simultaneously to increase intrathoracic pressure in unison. Referring to FIG. 3, output line 62 of system 10 may be connected to both bladder 68 (FIG. 2) and to a patient attachment tube 76 (FIG. 2A) using for example, a simple T connector 88 in line 62. Suitable adjustable flow constrictors 90 may be provided downstream of T connector 88 to properly apportion the flow of gas in line 62 between bladder 68 and patient connection tube 76.

The arrangement of FIG. 2A may be used independently as a cardiac output monitor when connected to a conventional respirator. In this regard, even if the only patient interface used for circulatory assist in accordance with the invention is the bladder of FIG. 2, the continuous cardiac output monitor of FIG. 2A is advantageously utilized to monitor the operation of the system, as more fully described below with reference to FIGS. 6A and 6B.

Referring to FIGS. 4A to 4E, the interrelationship of physiological parameters and the operation of the system of FIG. 1 is illustrated. From top to bottom, the traces represent the aortic pressure $A_O$, the electrocardiogram ECG, the square wave SQ activating the solenoid of valve 56, the ventilation breath $Q_v$ and the cardiac output $Q_F$ as measured by an electromagnetic flow probe. The operation of system 10 commences at time T. Before this time aortic pressure $A_o$ is low, indicating an insufficiency in cardiac output such as may be present in a patient with circulatory disease. The occurrence of a first QRS complex in the ECG following time T triggers the beginning of a time delay interval $t_d$. At the end of this delay interval (which can be anywhere in the range of from about 40 ms to about 200 ms, but is typically on the order of 100 ms) a square wave is provided to the solenoid of valve 56, thus opening valve 56. Valve 56 remains open for a period of time $t_{ip}$ (an inspiratory plateau time of typically 120 ms) determined by microcomputer 12. For every QRS complex in the ECG after time T, another square wave delayed by time $t_d$ and of width $t_{ip}$ is provided. The resulting pressure pulses in line 62 cause the patient's respiration to change from that of the normal respiratory cycle prior to time T to that of short, high frequency breaths occurring at a rate equal to that of the cardiac rate after time T. After such high frequency respiration commences (delayed in time with respect to ventricular ejection by a time corresponding to interval $t_d$) a substantial increase in cardiac output $Q_F$ is observed.

The operation of the system, as described above, is in a 1:1 respiration to cardiac rate mode. As illustrated in FIGS. 5A to 5E, this is not the only mode of operation. System 10, by suitable programming of microcomputer 12 (which is either manually selectable through information provided at keyboard 30, or may be automatically determined), can operate in a mode wherein one respiration pulse is provided for every N cardiac cycles. Typically N may be equal to 2. As represented in FIGS 5A to 5E, the transition from 1:1 to 1:2 operation occurs at time U. In the 1:2 mode there is a solenoid square wave SQ provided for every other QRS complex of the ECG waveform. The respiration $Q_v$ follows the solenoid square wave SQ. It will be understood that the depth of respiration required for supplying an adequate amount of oxygen will be larger for the 1:2 mode than for the 1:1 mode, and therefore a longer pulse width is appropriate. However, this consideration applies only if the embodiments of FIG. 2A or of FIG. 3 are used as the patient interface. If, on the other hand, the patient is breathing on his own or a separate respirator is provided, and a patient interface in accordance with FIG. 2 is used, no adjustment in the pulse width is required.

The use of a 1:2 mode is most appropriate when the patient has a rather rapid heartbeat. Due to inertia associated with the bulk transport of gas in the lungs, it is preferable that system 10 operates at an output pulse rate of approximately 40-60 per minute. Thus, if the patient has a heart rate greater than approximately 85 bpm, operation in the 1:2 mode may be appropriate. As illustrated in FIGS. 5A to 5E, the cardiac output $Q_F$ increases even further when the system is switched from the 1:1 mode to the 1:2 mode.

Figure 6A:
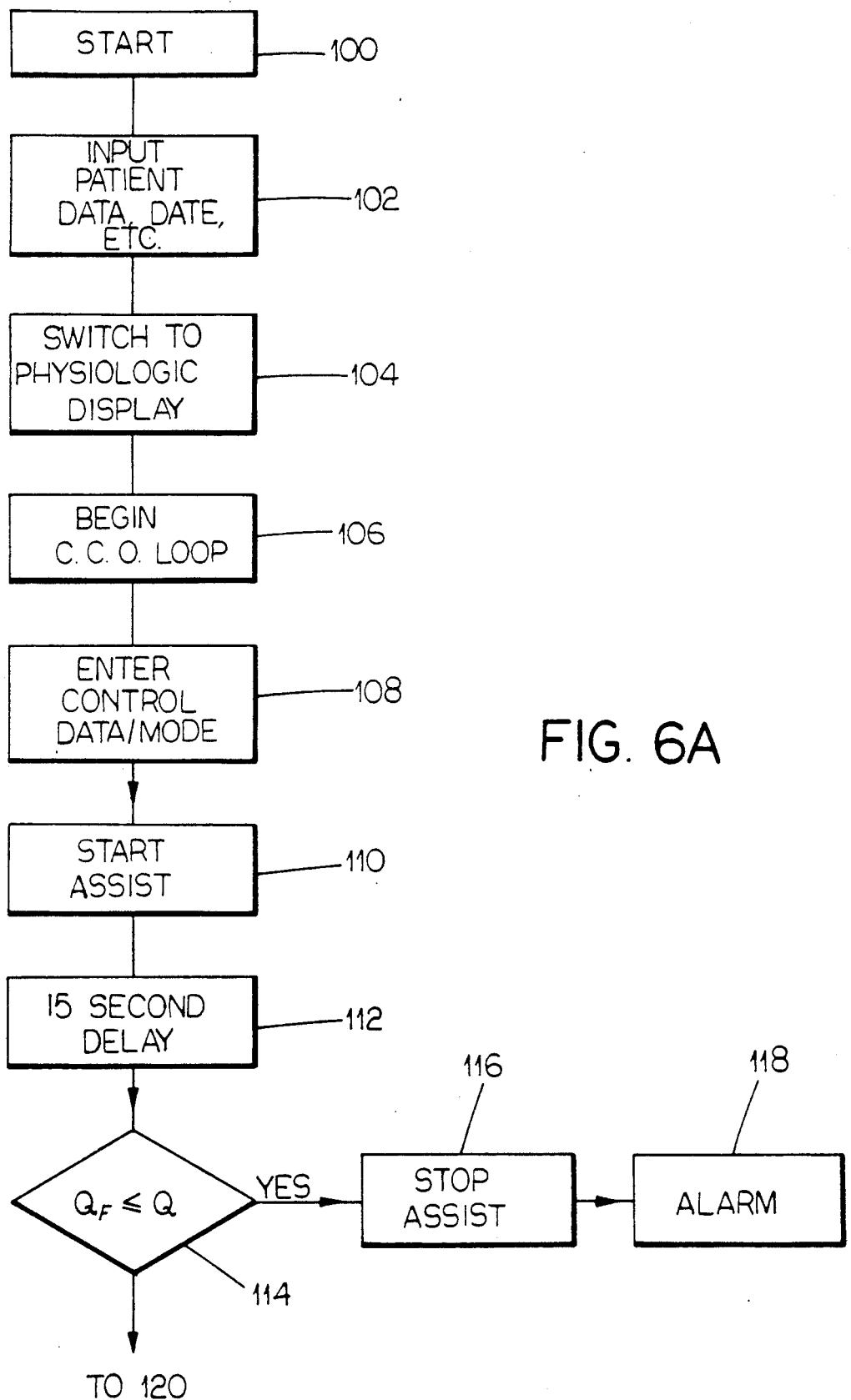
FIG. 6A and FIG. 6B are a flow chart of the program used by the microprocessor of the system of FIG. 1.
Figure 6B:
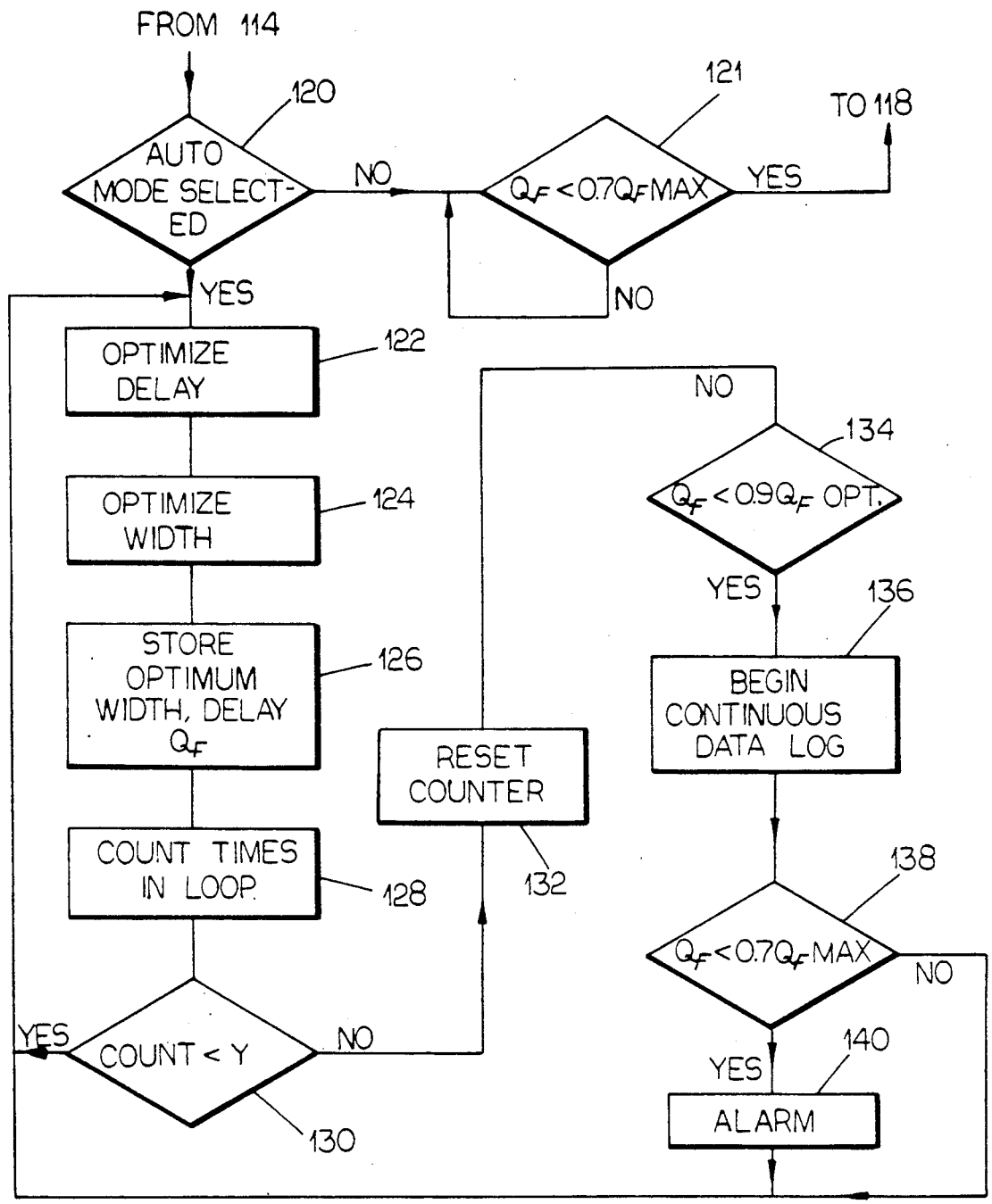

Referring to FIGS. 6A and 6B, a program for execution by microprocessor 20 of microcomputer 12 may be loaded from disk (not shown) into RAM 16 or may be permanently stored in ROM 18. At step 100, when the program is called up by using an appropriate entry on keyboard 30, the program is started by initializing all registers. An initial screen display is provided on display unit 28 so that data concerning the patient can be input to the system using keyboard 30 at step 102. Appropriate fields for the patient's name and other relevant data, (e.g. the date, the time, ECG lead selection etc.) are provided. After the last entry has been provided or, by default, if no data are provided, a switchover to a physiologic display occurs at step 104. At this point, if the electrocardiograph leads have been connected to the patient, the physician may view the patient's electrocardiogram on display 28. To assist the physician, the display may include a digital read-out of the patient's pulse rate.

At step 106 a loop (not separately shown) for monitoring the output of the continuous cardiac output monitor 66, which should have been connected to the patient, is started. As described above with respect to FIG. 2A, monitoring is accomplished by adding the entries in a first in/first out memory to determine the cardiac output of the patient. This loop operates continuously from this point forward with the current value being accessed from time to time as described below.

Microcomputer 12 may be programmed so that if the continuous cardiac output monitor 66 has not been connected, only continuous manual operation is permitted.

At step 108 a control mode and physician-selected control data may be entered. A decision may be made at this point to utilize manual control. In this case, the physician will enter a value for N of, for example, one or two to select the 1:1 or 1:2 mode respectively as described above. Further, selected values for $t_d$ and $t_{ip}$, in milliseconds, may be entered. Default values may be provided which are automatically entered if the data are not changed. After this data, which are placed in appropriate fields on the display of display unit 28, is checked, it is entered. The current value of cardiocirculatory output $Q_n$, as determined by continuous cardiac output monitor 66, is stored and system 10 starts to provide cardiocirculatory assistance at step 110. There is a delay at step 112 of approximately fifteen seconds to allow the system to operate and bring the patient to a new state of equilibrium. At step 114 a check is made to determine whether the output of continuous cardiac output monitor 66 (provided continuously by the loop initiated at step 106) indicates that the cardiac output of the patient is less than or equal to that just prior to the start of the assist at step 110. If for some reason the cardiac output has not increased, the assist is terminated at step 116 and an alarm is activated in the form of an audio tone emitted by display unit 28 as well as an appropriate visual alarm indication thereon (step 118). Thus, if the operation of system 10 does not provide increased cardiac output, the system operator is immediately alerted. It is then necessary either to restart the system and select different control data, or to check for the possibility of a system malfunction.

Assuming the assisted cardiac output is greater than the unassisted cardiac output, the program branches to step 120 where a determination is made as to whether the manual or automatic mode was selected. Assuming that the manual mode was selected, the program branches to step 121 where the output of the continuous cardiac output monitor 66 (as determined by the loop continuously running from the time of execution of step 106) is continuously monitored. As long as cardiac output is greater than 0.7 times the assisted cardiac output determined after step 114, operation of the system continues without any alarm being produced. This allows for some decrease in the assisted cardiac output due to, for example, the patient falling asleep. However, if cardiac output does decrease below 0.7 times the assisted value, the program branches to step 118 and the alarm is sounded. In this case, cardiocirculatory assistance is not automatically terminated.

Although not illustrated in FIGS. 6A and 6B, it is advantageous to provide a program interrupt at some point, such as during monitoring by step 122 so that the input data can be manually adjusted using the keyboard 30 to optimize cardiac output. This is advantageously accomplished while the system is providing circulatory assist and cardiac output is being monitored and displayed. After such manual optimization, it is appropriate to re-enter the program starting at step 108.

Figure 7:
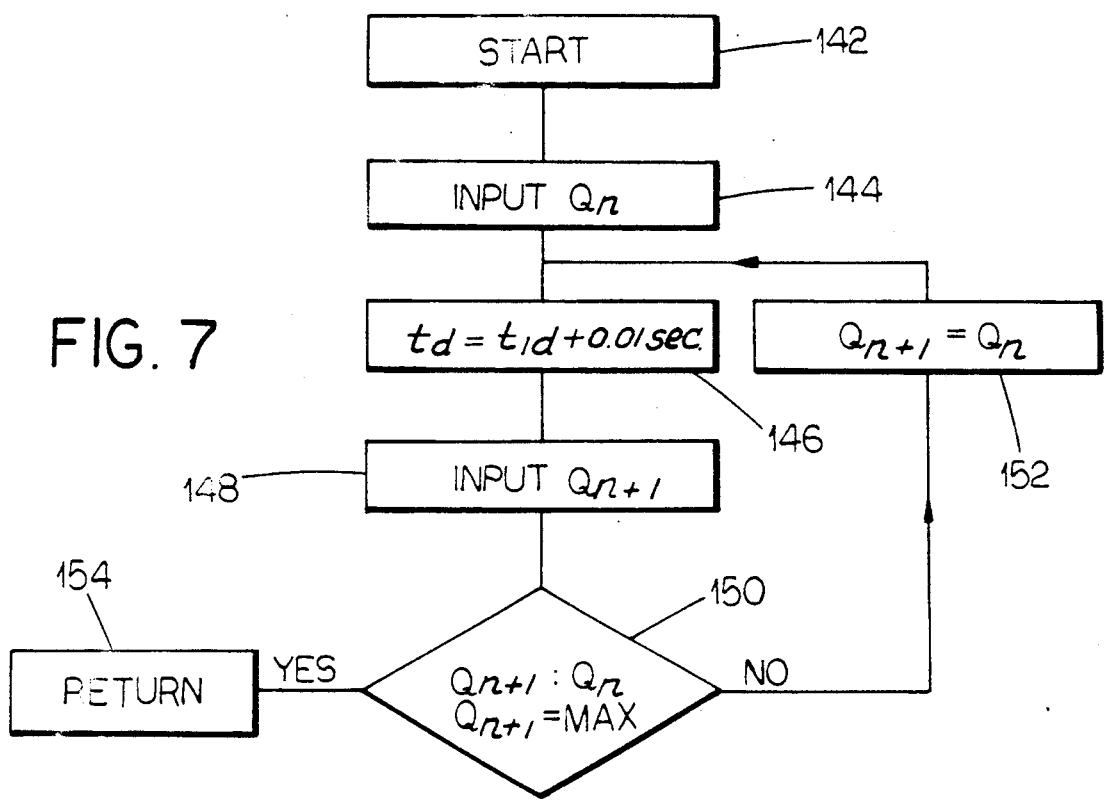
FIG. 7 is a flow chart of a first subroutine used in the flow chart of FIGS. 6A and 6B.
Figure 8:
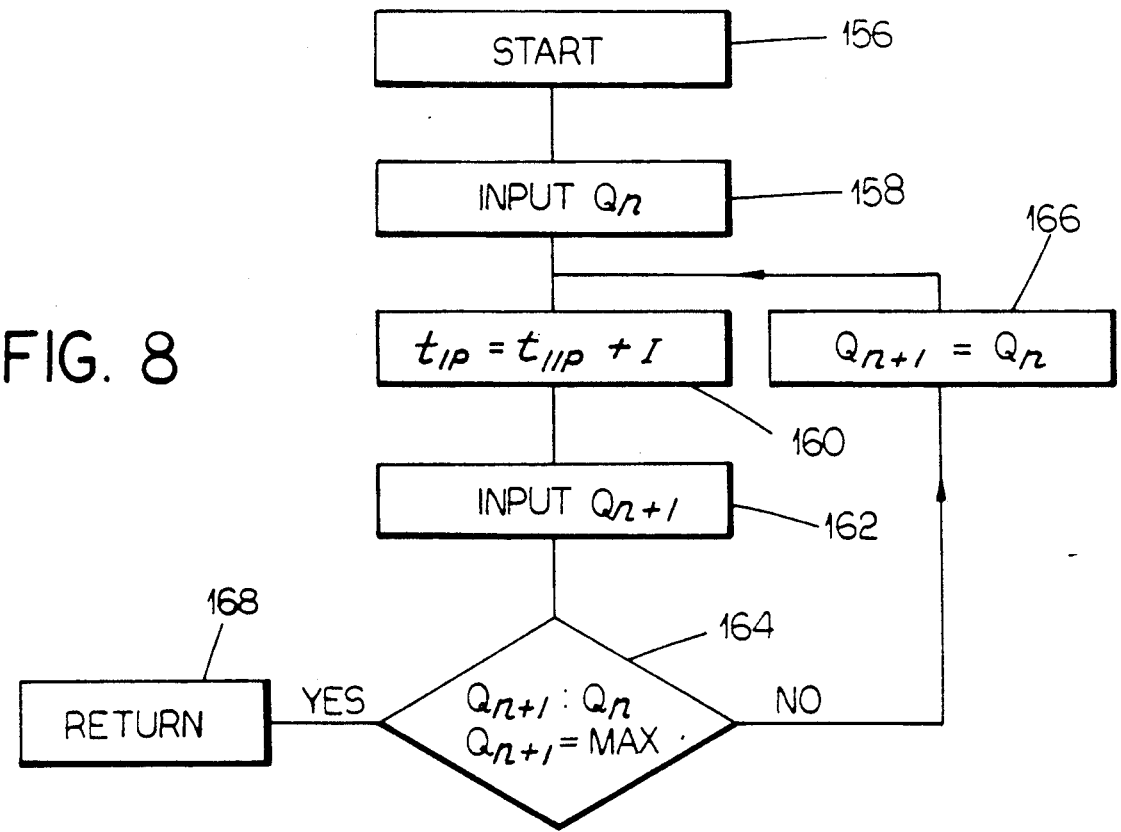
FIG. 8 is a flow chart of a second subroutine used in the flow chart of FIGS. 6A and 6B.

If the automatic mode of operation is selected, then branching from step 120 is to step 122, where a subroutine to automatically optimize delay time $t_d$, described below with respect to FIG. 7, is initiated. After the delay is optimized a subroutine which optimizes the inspiration pulse width $t_{ip}$, as described below with respect to FIG. 8, is executed at step 124. The optimum values of the delay time $t_d$, the pulse width $t_{ip}$ and cardiac output $Q_F$ are stored at 126.

The parameter which has been observed to be most critical in determining the extent of the cardiopulmonary circulatory assist provided is the delay time $t_d$ optimized at step 122. However, adjustment of the pulse width $t_{ip}$ at step 124 may also have an influence on cardiac output. Thus, it is advantageous to adjust the delay and width iteratively. This is performed by providing an adjustment loop. At step 128 a counter, initialized at a value of 0, is incremented by one count. At step 130 a determination is made as to whether the count is less than a predetermined integer Y which may have a value of, for example, two or three. Assuming that the present count at step 128 is less than the value of Y, the program loops back to step 122. The delay $t_d$ is then optimized at 122, the width $t_{id}$ is again optimized at 124 and the new optimum values including cardiac output, are stored at 126. The count is incremented at step 128. When the count is equal to Y, the program branches from step 130 to step 132 where the counter is reset. At step 134 cardiac output is continuously monitored to determine whether it has decreased below 0.9 times the optimum value stored at step 126. If this has occurred, the system begins at step 136 to log data into RAM 16. The data can also be stored on a disk in a disk drive. The data may include pulse rate, the output of the continuous cardiac output monitor 66 or any other relevant physiologic data, which is then available for later interpretation and review by the physician.

At step 138 a determination is made as to whether cardiac output has decreased below 0.7 times the maximum value $Q_{nMAX}$ (the maximum of the values stored at step 126) which occurred since circulatory assist was commenced, rather than the most recently stored value. As long as the answer is NO, the program loops back to step 122 and a reoptimization occurs. However, if the answer is YES an alarm is activated at step 140 prior to looping to step 122, since a decrease of more than 30% in cardiac output is considered sufficient cause to warrant investigation, rather than simply logging data.

Referring to FIG. 7 the delay optimization subroutine of step 122 is described. After initializing appropriate registers associated with the subroutine when starting at step 142, the current value of cardiac output $Q_n$ is stored at step 144. At step 146 an initial value of the delay time $t_{id}$ is incremented by ten milliseconds to provide a new value. The initial value may be manually entered at step 108 or may be a default value. In either case, this initial value should be chosen so as to be less than that anticipated as optimum. If this is the case, when the time delay is incremented at step 146 there will be an increase in cardiac output which is then provided as input $Q_{n+1}$ at step 148. At step 150 a comparison between the cardiac output $Q_n$ at step 144 and the cardiac output $Q_{n+1}$ at step 148 is made after a delay of at least two minutes to allow for establishing a new state of equilibrium. As long as the cardiac output has not decreased, the program loops to step 152 where the new value of $Q_n$ is set equal to that determined at step 148. Again the delay time is incremented at step 146 and the latest value of the cardiac output is accessed at step 148. The determination at step 150 is again made. The loop including steps 146, 148, 150 and 152 continues until an increment causes the cardiac output to drop slightly. At this time the program exits from the subroutine at 154. Although not shown, it is possible, if desired, to decrement the time delay by ten milliseconds just prior to exiting.

Referring to FIG. 8 a similar routine is followed with respect to the pulse width $t_{ip}$. After starting at step 156, the current cardiac output $Q_n$ is provided as an input at step 158. The initial inspiration plateau time $t_{iip}$ (initial pulse width or inspiration time) is incremented by a fixed value I such as ten milliseconds. At step 162 a new value for the cardiac output $Q_{n+1}$ is accessed. At step 164 a determination similar to that at step 150 is made. If the cardiac output has not decreased then the program branches to step 166 where the current value of cardiac output $Q_{n+1}$ is read in as the new value of $Q_n$. The pulse width is again incremented at step 160 and the program proceeds to step 162 and to step 164. The loop including steps 160, 162, 164 and 166 continues until such time as the cardiac output is determined, at step 164, to have decreased relative to the previous value. The subroutine is then exited at 168. As noted above with respect to FIG. 7, before exiting from the subroutine the inspiration pulse width may be decremented by an amount equal to the previous increment so that the cardiac output is maximized. However, in view of the relatively small changes being made, this step is not regarded as being critical, particularly with respect to the pulse width.

Various modifications of the invention will become apparent to those skilled in the art. For example, although not described herein it will be apparent that automatic selection of the value of N may be implemented. Thus, if the patient's heartbeat increases above some predetermined rate, it may be desirable to change from a 1:1 mode to a 1:2 mode. A lookup table of heart rate versus N value may be provided. However, it will be recognized that some hysteresis must be built in so that the mode change is not rapid and repetitive so as to produce discomfort in the patient. Further, as noted above, if the mode is changed, a change in the pulse width tip must occur as well in order to provide adequate ventilation if the apparatus of the invention is interfaced to the patient using the arrangement of FIG. 2A or FIG. 3.

The present invention is particularly well suited and most effective in providing cardiopulmonary circulatory assistance in patients having marginal circulation. In fact, the more difficulty the patient is experiencing, the greater will be the assist provided by the invention. In this regard the invention may be of critical importance in prolonging the lives of patients undergoing treatment for severe circulatory disorders.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention. For example, while the invention is advantageously implemented using a microcomputer, a manually controlled system may be implemented using discrete circuitry, including delay generators and a divide by N circuit. In addition, a hybrid approach, wherein such circuits are controlled by a microcomputer may also be implemented. Other equivalent approaches will occur to those skilled in the art.

We claim:

1. A method for providing circulatory assistance to a patient, comprising the steps of:
    detecting the onset of ventricular ejection in the cardiac cycle of the patient,
    continuously or periodically monitoring the patient's cardiac output on a breath by breath basis and providing output signals indicative thereof,
    selectively increasing intrathoracic pressure of the patient by injecting a respiratory fluid into the patient's lungs in relative phase with respect to said ventricular ejection, and
    repeatedly in response to said output signals adjusting said relative phase of pressure increase to ventricular ejection to maximize cardiac output by reducing ventricular afterload and maintaining ventricular preload.

2. The method of claim 1, wherein said step of selectively increasing said intrathoracic pressure is performed once every N cardiac cycles, where N is a positive integer.

3. The method of claim 2, wherein said positive integer is one or two.

4. The method of claim 1, further comprising the step of:
    adjusting the duration of a time interval for which said increasing of intrathoracic pressure occurs to maximize said cardiac output.

5. The method of claim 4, further comprising repeatedly adjusting said time interval duration concurrently with adjusting said relative phase to maximize said output.

6. The method of claim 1, wherein said step of monitoring said cardiocirculatory output comprises:
    determining oxygen uptake by the patient;
    determining the difference in arterial oxygen concentration and venous oxygen concentration; and
    dividing the oxygen uptake by said oxygen concentration difference to determine said cardiocirculatory output.

7. An apparatus for improving the cardiac output of a patient said apparatus comprising:
    detection means for detecting the onset of ventricular ejection in the cardiac cycle of the patient;
    pressure increasing means including means for injecting a respiratory fluid into the patient's lungs for selectively increasing intrathoracic pressure of the patient;
    control means responsive to said detection means for activating said pressure increasing means in relative phase with respect to said ventricular ejection;
    cardiocirculatory monitoring means for continuously or periodically monitoring the patient's cardiac output on a breath by breath basis and for providing output signals indicative thereof; and
    delay means responsive to said output signals for delaying activation of said control means in response to said detecting means and for thereby repeatedly adjusting said relative phase of pressure increase to ventricular ejection so that said cardiac output is maximized by reducing ventricular afterload and maintaining ventricular preload.

8. The apparatus of claim 7, wherein said cardiocirculatory monitoring means includes means for determining the rate of flow of blood from the heart.

9. The apparatus of claim 7, wherein said cardiocirculatory monitoring means includes an oxygen consumption monitoring means for determining the rate of oxygen consumption of the patient.

10. The apparatus of claim 9, wherein said oxygen consumption monitoring means comprises:
    means for supplying an oxygen stream to the patient,
    first concentration measuring means for measuring concentration of oxygen in said oxygen stream;
    second concentration measuring means for measuring concentration of oxygen in said stream at a point including gases exhausted by the patient; and
    flow measuring means for measuring the flow rate of gases in said stream.

11. The apparatus of claim 10, further comprising blood oxygen measuring means for measuring the difference in arterial oxygen concentration and venous oxygen concentration of the patient and for providing a difference output indicative of said difference in arterial oxygen concentration and venous oxygen concentration.

12. The apparatus of claim 11, further comprising calculating means for determining cardiac output; said calculating means including:
   difference means for determining the difference in said oxygen concentration measured by said first concentration measuring means and said second concentration measuring means;
   multiplying means for multiplying said difference in oxygen concentrations by said flow rate measured by said flow measuring means to determine a value of instantaneous oxygen consumption; and
   dividing means for dividing said value of instantaneous oxygen consumption by said difference output of said blood oxygen measuring means to determine a cardiac output value.

13. The apparatus of claim 12, further comprising integrating means for integrating values of said cardiac output to determine an averaged cardiac output.

14. The apparatus of claim 13, wherein said integrating means comprises:
   a first in/first out memory for storing said values of cardiac output; and
   means for determining the sum of said values in said memory.

15. The apparatus of claim 7, further comprising divider means responsive to said detection means, said divider means providing an output every N cardiac cycles, where N is a positive integer, and said control means being responsive to said output of said divider means.

16. The apparatus of claim 15, further comprising selection means for selecting said positive integer.

17. The apparatus of claim 16 wherein said positive integer may be selected by said selection means to be one or two.

18. The apparatus of claim 7, wherein said pressure increasing means comprises:
   a source of pressurized respiratory fluid;
   pressure pulse means for providing pulses of said pressurized respiratory fluid; and
   a patient interface means for utilizing said pulses to increase said intrathoracic pressure.

19. The apparatus of claim 18, wherein said pressurized respiratory fluid is air or an air/oxygen mixture and said patient interface means includes a tube for supplying said pressure pulses to the lungs for inspiration by the patient.

20. An apparatus for improving the cardiac output of a patient, said apparatus comprising:
   detection means for detecting the onset of ventricular ejection in the cardiac cycle of the patient;
   continuously or periodically monitoring means for monitoring the patient's cardiac output on a breath by breath basis,
   pressure increasing means including means for injecting a respiratory fluid into the patient's lungs for selectively increasing intrathoracic pressure of the patient; and
   control means responsive to said detection means for activating said pressure increasing means in relative phase with respect to said ventricular ejection and for repeatedly adjusting said relative phase of pressure increase to ventricular ejection to maximize cardiac output by reducing ventricular afterload and maintaining ventricular preload.

21. An apparatus for improving the cardiac output of a patient, said apparatus comprising:
   detection means for detecting the onset of ventricular ejection in the cardiac cycle of the patient;
   pressure increasing means for selectively increasing, intrathoracic pressure of the patient;
   control means responsive to said detection means for activating said pressure increasing means in relative phase with respect to said ventricular ejection;
   cardiocirculatory monitoring means for ascertaining the extent of cardiac output improvement and for providing an output signal indicative thereof, said cardiocirculatory monitoring means including oxygen consumption monitoring means for determining the rate of oxygen consumption of the patient, and said oxygen consumption monitoring means comprising (i) means for supplying an oxygen stream to the patient, (ii) first concentration measuring means for measuring concentration of oxygen in said oxygen stream, (iii) second concentration measuring means for measuring concentration of oxygen in said stream at a point including gases exhausted by the patient, and (iv) flow measuring means for measuring the flow rate of gases in said stream, said cardiocirculatory monitoring means including calculating means responsive to said means (i)–(iv) for producing said output signal, and
   delay means responsive to said output signal, said delay means being for delaying activation of said control means in response to said detecting means so that said cardiac output is maximized.

22. The apparatus of claim 21, further comprising blood oxygen measuring means for measuring the difference in arterial oxygen concentration and venous oxygen concentration of the patient and for providing a difference output indicative of said difference in arterial oxygen concentration and venous oxygen concentration.

23. The apparatus of claim 22, wherein, said calculating means comprises:
   difference means for determining the difference in oxygen concentration measured by said first concentration measuring means and said second concentration measuring means;
   multiplying means for multiplying said difference by said flow rate measured by said flow measuring means to determine a value of instantaneous oxygen consumption; and
   dividing means for dividing said value of instantaneous oxygen consumption by said difference output of said blood oxygen measuring means to determine a cardiac output value.

24. The apparatus of claim 23, further comprising integrating means for integrating values of said cardiac output to determine an averaged cardiac output.

25. The apparatus of claim 24, wherein said integrating means comprises:
   a first in/first out memory for storing said values of cardiac output; and
   means for determining the sum of said values in said memory.

* * * * *

UNITED STATES PATENT AND TRADEMARK OFFICE
CERTIFICATE OF CORRECTION

PATENT NO. : 5,020,516

DATED : June 4, 1991

INVENTOR(S) : James W. Biondi, Richard A. Mentelos

It is certified that error appears in the above-identified patent and that said Letters Patent is hereby corrected as shown below:

Column 4, line 5, "achieving ability. Further," should read --archiving ability. Further,--.

Column 6, line 25, "on an almost a breath by breath, i.e., instantaneous," should read --on a breath by breath, i.e., an almost instantaneous,--.

Column 10, line 61, "tip" should read --$t_{ip}$--.

Column 11, line 28, "tip" should read --$t_{ip}$--.

Column 13, line 9, "concentration" should read --concentrations--.

UNITED STATES PATENT AND TRADEMARK OFFICE
CERTIFICATE OF CORRECTION

PATENT NO. : 5,020,516
DATED : June 4, 1991
INVENTOR(S) : James W. Blondi, et al It is certified that error appears in the above-indentified patent and that said Letters Patent is hereby corrected as shown below:

Column 13, line 56, "continuously or periodically monitoring means for monitoring" should read --monitoring means for continuously or periodically monitoring--.

Signed and Sealed this

First Day of March, 1994

Attest:

BRUCE LEHMAN

*Attesting Officer*  *Commissioner of Patents and Trademarks*